United States Patent
Jacques et al.

(10) Patent No.: US 6,664,226 B2
(45) Date of Patent: *Dec. 16, 2003

(54) SPHERICAL COMPACTED UNIT DOSE SOFTENER

(75) Inventors: Alain Jacques, Blegny (BE); Juliette Rousselet, Liege (BE); Hoai-Chau Cao, Liege (BE)

(73) Assignee: Colgate-Palmolive Co, New York, NY (US)

( * ) Notice: Subject to any disclaimer, the term of this patent is extended or adjusted under 35 U.S.C. 154(b) by 154 days.

This patent is subject to a terminal disclaimer.

(21) Appl. No.: 10/054,334

(22) Filed: Jan. 22, 2002

(65) Prior Publication Data

US 2002/0169094 A1 Nov. 14, 2002

Related U.S. Application Data

(63) Continuation-in-part of application No. 09/821,233, filed on Mar. 29, 2001, now abandoned, which is a continuation-in-part of application No. 09/558,822, filed on Apr. 26, 2000, now Pat. No. 6,258,767.

(51) Int. Cl.$^7$ ............................................... C11D 17/00
(52) U.S. Cl. ........................ 510/521; 510/298; 510/446; 510/507
(58) Field of Search ................................. 510/295, 298, 510/505, 506, 507, 521, 446

(56) References Cited

U.S. PATENT DOCUMENTS

| | | | | |
|---|---|---|---|---|
| 4,752,408 A | * | 6/1988 | Koester et al. | 510/296 |
| 5,225,100 A | * | 7/1993 | Fry et al. | 510/298 |
| 5,376,287 A | * | 12/1994 | Borcher et al. | 510/519 |
| 5,658,874 A | * | 8/1997 | Davies et al. | 510/446 |
| 5,759,988 A | * | 6/1998 | Heile et al. | 510/441 |
| 5,955,057 A | * | 9/1999 | Maunder et al. | 424/44 |
| 6,110,886 A | * | 8/2000 | Scepanski | 510/515 |
| 6,159,926 A | * | 12/2000 | Crutzen et al. | 510/515 |
| 6,258,767 B1 | * | 7/2001 | Jacques et al. | 510/298 |

* cited by examiner

Primary Examiner—John Hardee
(74) Attorney, Agent, or Firm—Bernard Lieberman

(57) ABSTRACT

A unit dose laundry composition for softening or conditioning fabrics which is suitable as an additive to the wash cycle of an automatic washing machine, said unit dose composition comprising a compacted granular composition comprising a fabric softener or a fabric conditioner, said compacted granular composition being characterized by having a spherical shape and having no discrete outer layer surrounding said fabric softener or conditioner, which outer layer is comprised of an alkaline material such that the pH of the wash water is increased upon the dissolution of said outer layer in said wash water.

9 Claims, No Drawings

SPHERICAL COMPACTED UNIT DOSE SOFTENER

This application is a continuation-in-part of application Ser. No. 09/821,233 filed Mar. 29, 2001 now abandonded which in turn is a continuation-in-part of Ser. No. 09/558,822 filed Apr. 26, 2000, now U.S. Pat. No. 6,258,767, the disclosures of which are incorporated herein by reference.

FIELD OF THE INVENTION

This invention relates to wash cycle unit dose laundry compositions for softening or conditioning fabrics. More particularly, this invention relates to unit dose fabric softening compositions which are compacted granular compositions spherical in shape and suitable for use in the wash cycle of an automatic washing machine.

BACKGROUND OF THE INVENTION

Detergent compositions manufactured in the form of tablets of compacted detergent powder are known in the art. U.S. Pat. No. 5,225,100, for example, describes a tablet of compacted powder comprising an anionic detergent compound which will adequately disperse in the wash water.

Although detergent compositions shaped as tablets have received much attention in the patent literature, the use of such tablets to provide a unit dose fabric softener which will soften or condition fabrics without impairing detergency is not known.

One possible option for providing a unit dose softener is to introduce the softening ingredients directly into the rinse cycle. But, for this type of product to be effective several practical requirements must be met. To begin with, the size and shape of the unit dose container must be readily compatible with the geometry of a wide variety of rinse cycle dispensers designed for home washing machines in order to insure its easy introduction into the dispenser.

Further, the unit dose composition must be formulated to readily dispense its contents upon contact with water in a period of time corresponding to the residence time of the unit dose in the dispenser, namely, the period of time during which water enters and flows through the rinse cycle dispenser. The aforementioned practical requirements have to date not been successfully met and therefore there remains a need in the art for a commercially acceptable unit dose softener capable of activation in the rinse cycle.

Wash cycle softeners are known in the art which condition fabrics during the period of the wash cycle. Tablet unit doses for detergent compositions are also known. Such tablets are typically flat compacted unit compositions which conceptually offer numerous advantages to the consumer such as: ease of dosing; cleaner wash cycle dispensers resulting from not being dosed with loose powder; less bulk to carry and dispense; ease of handling relative to liquids; and environmental benefits attendant to reduced packaging requirements.

But, despite these advantages, there is a major drawback which occurs in front loading washing machines which represent at least 90% of the European market, and are gaining in consumer acceptance in North America. In front loading machines, a flat compacted object when introduced into the wash cycle often becomes trapped within a few minutes in the rubber seal surrounding the window of the washing machine. Once trapped in the seal, the tablet tends to remain trapped until the wash cycle is over and is consequently not dispersed in the wash water. To overcome this problem, different approaches have been taken.

Some tablet manufacturers provide a net or sachet designed to contain the tablet unit dose, and thereby avoid the problem of direct contact between the tablet and the seal. Another proposed solution involves providing a rapidly dispersible tablet in the wash water by incorporating an effervescent matrix and/or a disintegration agent into the tablet. But, these proposed options are generally uneconomical and often result in an unduly fragile tablet unable to readily withstand normal handling by the consumer without fracturing. Thus, there is a need for an economical unit dose tablet capable of providing conditioning of fabrics, and which retains its physical integrity during normal handling prior to being introduced into the washing machine.

SUMMARY OF THE INVENTION

The present invention provides a non-foaming unit dose laundry composition for softening or conditioning fabrics which is suitable as an additive to the wash cycle of an automatic washing machine, said unit dose composition comprising a compacted granular composition comprising a fabric softener or a fabric conditioner, said compacted granular composition being characterized by having a spherical shape and having no discrete outer layer surrounding said fabric softener or conditioner, which outer layer is comprised of an alkaline material such that the pH of the wash water is increased upon the dissolution of said outer layer in said wash water, said unit dose laundry composition being free of (i) a soap surfactant; and (ii) a quaternary ammonium compound fabric softener; and containing less than about 5%, by weight, of sodium bicarbonate, and less than about 2%, by weight, of an organic acid.

In a preferred embodiment of the invention the fabric softener or conditioner is comprised of a fabric softening clay and an organic fatty softening material. Especially preferred fabric softeners comprise a clay mineral softener, such as bentonite, in combination with a pentaerythritol compound as further described herein. Useful combinations of such softener may very from about 83%, to about 90%, by weight, of clay, and from about 10% to about 17%, by weight, of fatty softening material such as a pentaerythritol compound (often abbreviated herein as "PEC").

In a further preferred embodiment of the invention the fabric softener or conditioner is free of a soap surfactant. The unit dose composition is also most preferably free of sodium bicarbonate but may contain up to an amount below about 5%, by weight, thereof. It also preferably contains less than about 2%, by weight, of organic acid and most preferably less than about 1%, by weight.

In accordance with the process aspect of the invention there is provided a process for softening or conditioning laundry which comprises contacted the laundry with an effective amount of the unit dose laundry composition defined above.

DETAILED DESCRIPTION OF THE INVENTION

The clays that are useful components of the invented products are those which cooperate with the organic fatty softener materials to provide enhanced softening of laundry. Such clays include the montmorillonite-containing clays which have swelling properties (in water) and which are of smectite structure, so that they deposit on fibrous materials, especially cotton and cotton/synthetic blends, such as cotton/polyester, to give such fibers and fabrics made from them a surface lubricity or softness. The best of the smectite clays for use in the present invention is bentonite and the best of the bentonites are those which have a substantial swelling capability in water, such as the sodium and potassium bentonites. Such swelling bentonites are also known as western or Wyoming bentonites, which are essentially sodium bentonite. Other bentonites, such as calcium bentonite, are normally non-swelling and usually are, in themselves, unacceptable as fabric softening agents. However, it has been found that such non-swelling bentonites exhibit even better fabric softening in combination with PEC's than do the swelling bentonites, provided that there is present in the softening composition, a source of alkali metal or other solubilizing ion, such as sodium (which may come from sodium hydroxide, added to the composition, or from sodium salts, such as builders and fillers, which may be functional components of the composition). Among the preferred bentonites are those of sodium and potassium, which are normally swelling, and calcium and magnesium, which are normally non-swelling. Of these it is preferred to utilize calcium (with a source of sodium being present) and sodium bentonites. The bentonites employed may be produced in the United States of America, such as Wyoming bentonite, but also may be obtained from Europe, including Italy and Spain, as calcium bentonite, which may be converted to sodium bentonite by treatment with sodium carbonate, or may be employed as calcium bentonite. Also, other montmorillonite-containing smectite clays of properties like those of the bentonites described may be substituted in whole or in part for the bentonites described herein and similar fabric softening results will be obtained.

The swellable bentonites and similarly operative clays are of ultimate particle sizes in the micron range, e.g., 0.01 to 20 microns and of actual particle sizes in the range of No's. 100 to 400 sieves, preferably 140 to 325 sieves, U.S. Sieve Series. The bentonite and other such suitable swellable clays may be agglomerated to larger particle sizes too, such as 60 to 120 sieves, but such agglomerates are not preferred unless they include the PEC('s) too (in any particulate products).

A main component of the invented compositions and articles of the present invention, and which is used in combination with the fabric softening clay is an organic fatty softener. The organic softener can be anionic or nonionic fatty chains ($C_{10}$–$C_{22}$ preferably $C_{12}$–$C_{18}$). Anionic softeners include fatty acids soaps. Preferred organic softeners are nonionics such as fatty esters, ethoxylated fatty esters, fatty alcohols and polyols polymers. The organic softener is most preferably a higher fatty acid ester of a pentaerythritol compound, which term is used in this specification to describe higher fatty acid esters of pentaerythritol oligomers, higher fatty acid esters of pentaerythriol and higher fatty acid esters of lower alkylene oxide derivatives of pentaerythritol oligomers. Pentaerythritol compound is often abbreviated as PEC herein, which description and abbreviation may apply to any or all of pentaerythritol, oligomers, thereof and alkoxylated derivatives thereof, as such, or more preferably and more usually, as the esters, as may be indicated by the context.

The oligomers of pentaerythritol are preferably those of two to five pentaerythritol moieties, more preferably 2 or 3, with such moieties being joined together through etheric bonds. The lower alkylene oxide derivatives thereof are preferably of ethylene oxide or propylene oxide monomers, dimers or polymers, which terminate in hydroxyls and are joined to the pentaerythritol or oligomer of pentaerythritol through etheric linkages. Preferably there will be one to ten alkylene oxide moieties in each such alkylene oxide chain, more preferably 2 to 6, and there will be one to ten such groups on a PEC, depending on the oligomer. At least one of the PEC OH groups and preferably at least two, e.g., 1 or 2 to 4, are esterified by a higher fatty acid or other higher aliphatic acid, which can be of an odd number of carbon atoms.

The higher fatty acid esters of the pentaerythritol compounds are preferably partial esters. And more preferably there will be at least two free hydroxyls thereon after esterification (on the pentaerythritol, oligomer or alkoxyalkane groups). Frequently, the number of such free hydroxyls is two or about two but sometimes it may by one, as in pentaerythritol tristearate, or as many as eight, as in pentaerythritol tetrapalmitate. The higher aliphatic or fatty acids that may be employed as esterifying acids are those of carbon atom contents in the range of 8 to 24, preferably 12 to 22 and more preferably 12 to 18, e.g., lauric, myristic, palmitic, oleic, stearic and behenic acids. Such may be mixtures of such fatty acids, obtained from natural sources, such as tallow or coconut oil, or from such natural materials that have been hydrogenated. Synthetic acids of odd or even numbers of carbon atoms may also be employed. Of the fatty acids lauric and stearic acids are often preferred, and such preference may depend on the pentaerythritol compound being esterified.

Examples of some esters (PEC's) within the present invention follow:

Monopentaerythritol Esters

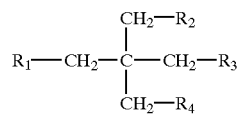

Monopentaerythritol Dilaurate

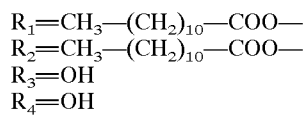

$R_1$=$CH_3$—$(CH_2)_{10}$—COO—
$R_2$=$CH_3$—$(CH_2)_{10}$—COO—
$R_3$=OH
$R_4$=OH

Monopentaerythritol Monostearate $R_1$=$CH_3$—$(CH_2)_{16}$—COO—
$R_2$=OH
$R_3$=OH
$R_4$=OH Monopentaerythritol Distearate $R_1$=$CH_3$—$(CH_2)_{16}$—COO—
$R_2$=$CH_3$—$(CH_2)_{16}$—COO—
$R_3$=OH
$R_4$=OH Monopentaerythritol Tristearate $R_1$=$CH_3$—$(CH_2)_{16}$—COO—
$R_2$=$CH_3$—$(CH_2)_{16}$—COO—
$R_3$=$CH_3$—$(CH_2)_{16}$—COO—
$R_4$=OH Monopentaerythritol Monobehenate $R_1$=$CH_3$—$(CH_2)_{20}$—COO—
$R_2$=OH
$R_3$=OH $R_4$=OH Monopentaerythritol Dibehenate $R_1$=CH$_3$—(CH$_2$)$_{20}$—COO—
$R_2$=CH$_3$—(CH$_2$)$_{20}$—COO—
$R_3$=OH
$R_4$=OH Dipentaerythritol Esters

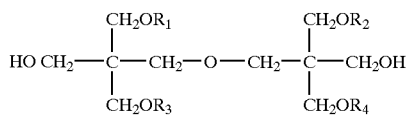

Dipentaerythritol Tetralaurate $R_1$=CH$_3$—(CH$_2$)$_{10}$—CO
$R_2$=CH$_3$—(CH$_2$)$_{10}$—CO
$R_3$=CH$_3$—(CH$_2$)$_{10}$—CO
$R_4$=CH$_3$—(CH$_2$)$_{10}$—CO Dipentaerythritol Tetrastearate $R_1$=CH$_3$—(CH$_2$)$_{16}$—CO
$R_2$=CH$_3$—(CH$_2$)$_{16}$—CO
$R_3$=CH$_3$—(CH$_2$)$_{16}$—CO
$R_4$=CH$_3$—(CH$_2$)$_{16}$—CO Pentaerythritol 10 Ethylene Oxide Ester

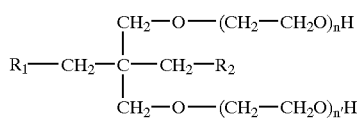

with n+n'=10

Monopentaerythritol 10 Ethylene Oxide Distearate $R_1$=CH$_3$—(CH$_2$)$_{16}$—COO—
$R_2$=CH$_3$—(CH$_2$)$_{16}$—COO—

Pentaerythritol 4 Propylene Oxide Esters

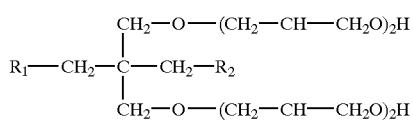

Monopentaerythritol 4 Propylene Oxide Monostearate $R_1$=CH$_3$—(CH$_2$)$_{16}$—COO—
$R_2$=OH Monopentaerythritol 4 Propylene Oxide Distearate $R_1$=CH$_3$—(CH$_2$)$_{16}$—COO—
$R_2$=CH$_3$—(CH$_2$)$_{16}$—COO—

Although in the formulas given herein some preferred pentaerythritol compounds that are useful in the practice of this invention are illustrated it will be understood that various other such pentaerythritol compounds within the description thereof herein may be employed too, including such as pentaerythritol dihydrogenated tallowate, pentaerythritol ditallowate, pentaerythritol dipalmitate, and dipentaerythritol tetratallowate.

Other fabric softening materials may be incorporated into the presently described unit dose laundry compositions provided they are not ecologically unacceptable and if they do not interfere with the fiber softening action of the clay and organic fatty softener material. In fact, sometimes, when antistatic action is desirable in the product, such additions may be important because although PEC's, for example, have some antistatic properties it is generally insufficient for the intended purposes. Thus, it is possible to formulate fabric softening compositions and articles with the PEC supplemented by other antistatic agents and also by fabric softeners. The foremost of such antistatic materials are the quaternary ammonium salts but when they are present there can be ecological problems, due to their alleged toxicities to aquatic organisms. Other antistats and fabric softeners include: higher alkyl neoalkanamides, e.g., N-stearyl neodecanamide; isostearamides; amines, such as N,N-ditallowalkyl N-methyl amine; esterified quaternary salts or esterquats: amidoamines; amidoquats; imidazolines; imidazolinium salts.

Other useful ingredients for the unit dose laundry compositions of the invention include disintegration materials to enhance the disintegration of the unit dose in the wash water. Such materials include an effervescent matrix such as citric acid combined with baking, soda, or materials such as PVP polymer and cellulose. Granulating agents may be used such as polyethylene glycol; bactericides, perfumes, dyes and materials to protect against color fading, dye transfer, anti-pilling and anti-shrinkage. For purposes of enhancing the aesthetic properties of the final composition, cosmetic ingredients such as dyes, micas and waxes may be used as coating ingredients to improve the appearance and feel of the unit dose.

EXAMPLE 1

A unit dose composition was prepared from the following ingredients:

|  | Weight Percent |
| --- | --- |
| Clay/Pentaerythritol ditallowate (PDT) in a ratio of 83%:17% | 80% |
| Effervescent matrix of baking soda and citric acid | 17% |
| Polyvinylpyrrolidone | 1% |
| Perfume | 2% |
| Dye | 0.03% |

This method of manufacture consisted of mixing all the ingredients with the exception of perfume in a Loedige-type mixer. The resulting blend was dried in an oven and perfume was then added to the dried powder. The powder was then compacted using an alternative or rotative press mounted with appropriate dyes. The weight of the spherical unit dose was 60 g and such unit dose dispersed in water within 20 minutes when introduced in the wash load at the beginning of the wash in a European Miele W832 front loading washing machine set a Program White Colors at 40° C.

The softness provided by the unit dose compositions on terry towels, cotton tee-shirts and cotton kitchen towels was evaluated after cummulative washes and compared with a commercial liquid fabric softener. A 3 Kg laundry ballast was used in the machine. Softness was evaluated by a panel of six judges using 9 replicates. The results were as follows:

SOFTNESS EVALUATION

| Laundry Item | Softness Comparison |
|---|---|
| Terry towels | 1 unit dose softener composition of the invention provided equivalent softness to commercial liquid FS after 10 cumulative wash cycles |
| Cotton tee-shirts | 1 unit dose softener provided equivalent softness to commercial liquid FS after one wash cycle |
| Cotton kitchen towels | 1 unit dose softener provided enhanced softening relative to commercial liquid FS after one wash cycle |

EXAMPLE 2

Unit dose softener compositions were prepared as described in Example 1 to provide 60 gram spherical softeners having a diameter of 44 mm. The typical range of spherical dose diameters is from about 5 to about 60 mm; preferably from about 20 to about 40 mm; and most preferably from about 30 to about 35 mm. The dissolution behavior of the unit dose softener in the washing machine was compared to a compacted tablet of 35 grams. The European washing machine and conditions of laundering were as described in Example 1. The spherical unit dose softener of the invention and the tablet were introduced into the washing machine before the start of the wash. Results were as follows:

Dispersion Evaluation

Both the spherical unit dose and the tablet became entrapped in the rubber gasket of the washing machine within a few minutes of the wash cycle. However, the spherical unit dose was able to readily disengage itself from the gasket and return to the laundry while the tablet remained trapped in the gasket.

Out of ten wash cycles, the tablet was trapped in the rubber gasket of the machine every time (ten times). The average time to get stuck was about 10 minutes. In contrast thereto, out of ten wash cycles, the spherical unit dose softener never was trapped in the rubber gasket and dissolved in the wash water without difficulty.

What is claimed is:

1. A non-foaming unit dose laundry composition for softening or conditioning fabrics which is suitable as an additive to the wash cycle of an automatic washing machine, said unit dose composition comprising a compacted granular composition comprising a fabric softener or a fabric conditioner, said compacted granular composition being characterized by having a spherical shape and having no discrete outer layer surrounding said fabric softener or conditioner, which outer layer is comprised of an alkaline material such that the pH of the wash water is increased upon the dissolution of said outer layer in said wash water, said unit dose laundry composition being free of (i) a soap surfactant; and (ii) a quaternary ammonium compound fabric softener; and containing less than about 5%, by weight, of sodium bicarbonate, and less than about 2%, by weight, of an organic acid.

2. A unit dose laundry composition as in claim 1 wherein said fabric softener or fabric conditioner comprises a softening clay in combination with an organic fatty softening material.

3. A unit dose laundry composition as in claim 2 wherein said softening clay is a montmorillonite-containing clay and said organic fatty softening material is a pentaerythritol compound ("PEC") selected from the group consisting of a higher aliphatic acid ester of pentaerythritol, an oligomer of pentaerythritol, a lower alkylene oxide derivative of an oligomer of pentaerythritol, and a mixture thereof.

4. A unit dose laundry composition as in claim 2 wherein said softening clay is at least partially coated with said organic fatty softening material and serves as a carrier for such fatty softening material.

5. A unit dose laundry composition as in claim 2 wherein said softening clay is bentonite and said PEC is a higher aliphatic ester of pentaerythritol or of an oligomer of pentaerythritol.

6. A unit dose laundry composition as in claim 5 which comprises, by weight, from about 83% to about 90% of bentonite and from about 10% to about 17% of said PEC.

7. A process for softening or conditioning laundry which comprises contacting the laundry with an effective amount of the unit dose composition of claim 1.

8. A process according to claim 7 wherein the fabric softener comprises a softening clay in combination with an organic fatty softening material.

9. A process according to claim 8 wherein said softening clay is bentonite and said organic softening material comprises a pentaerythritol compound (PEC) selected from the group consisting of a higher aliphatic acid ester of pentaerythritol, an oligomer of pentaerythritol, a lower alkylene oxide derivative of an oligomer of pentaerythritol, and a mixture thereof.

* * * * *